US010238332B2

(12) United States Patent
Jang et al.

(10) Patent No.: US 10,238,332 B2
(45) Date of Patent: Mar. 26, 2019

(54) WRINKLE MEASUREMENT APPARATUS AND WRINKLE MEASUREMENT METHOD

(71) Applicant: AMOREPACIFIC CORPORATION, Seoul (KR)

(72) Inventors: Sue Im Jang, Yongin-si (KR); Eun Joo Kim, Yongin-si (KR); Hae Kwang Lee, Yongin-si (KR); Yeong Min Yeon, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 15/323,220

(22) PCT Filed: Jun. 26, 2015

(86) PCT No.: PCT/KR2015/006578
§ 371 (c)(1),
(2) Date: Dec. 30, 2016

(87) PCT Pub. No.: WO2016/003123
PCT Pub. Date: Jan. 7, 2016

(65) Prior Publication Data
US 2017/0127998 A1    May 11, 2017

(30) Foreign Application Priority Data

Jul. 2, 2014  (KR) .................. 10-2014-0082504

(51) Int. Cl.
*A61B 5/00* (2006.01)
*A61B 5/103* (2006.01)
*A61B 5/107* (2006.01)

(52) U.S. Cl.
CPC .............. *A61B 5/442* (2013.01); *A61B 5/103* (2013.01); *A61B 5/1075* (2013.01);
(Continued)

(58) Field of Classification Search
CPC ..... A61B 5/442; A61B 5/1075; A61B 5/1077; A61B 5/1079; G06K 7/00; G06K 9/00
See application file for complete search history.

(56) References Cited

U.S. PATENT DOCUMENTS 5,474,070 A * 12/1995 Ophir .................. A61B 5/0048
600/437
8,175,689 B2 * 5/2012 Hunter-Jones ......... A61B 5/442
356/244

(Continued)

FOREIGN PATENT DOCUMENTS

JP  WO 2014156461 A1 * 10/2014 ........... A61B 5/0077
KR  10-2010-0003668 A    1/2010
KR  10-2012-0128756 A   11/2012

OTHER PUBLICATIONS

Kuwazuru, Osamu, Miyamot, Kukizo, Yoshikawa, Nobuhiro, Imayama Shuehi. "Skin Wrinkling morphology changes suddenly in early 30s" Skin Res Technolocy, Nov. 2012.*

(Continued)

*Primary Examiner* — Kim Y Vu
*Assistant Examiner* — Molly Delaney
(74) *Attorney, Agent, or Firm* — Merchant & Gould P.C.

(57) ABSTRACT

The present invention relates to a wrinkle measurement apparatus and a wrinkle measurement method. The wrinkle measurement apparatus according to one embodiment of the present invention comprises: a surface direction compression part including first and second contact parts arranged at a preset gap while coming into close contact with the skin, so as to compress the skin in the direction of the surface thereof; and a wrinkle measuring part for measuring skin wrinkles in at least two states among pre-compression, mid-compression and post-compression.

6 Claims, 6 Drawing Sheets

(52) U.S. Cl.
CPC .......... *A61B 5/1077* (2013.01); *A61B 5/1079* (2013.01); *A61B 5/0053* (2013.01); *A61B 2576/02* (2013.01)

(56) References Cited

U.S. PATENT DOCUMENTS

2008/0304736 A1* 12/2008 Nakagawa ............ A61B 5/0059
　　　　　　　　　　　　　　　　382/165
2013/0079643 A1*  3/2013 Korichi ................. A61B 5/442
　　　　　　　　　　　　　　　　600/474

OTHER PUBLICATIONS

International Search Report for PCT/KR2015/006578, dated Sep. 1, 2015.
Written Opinion for PCT/KR2015/006578, dated Sep. 1, 2015.

* cited by examiner

[FIG. 1]
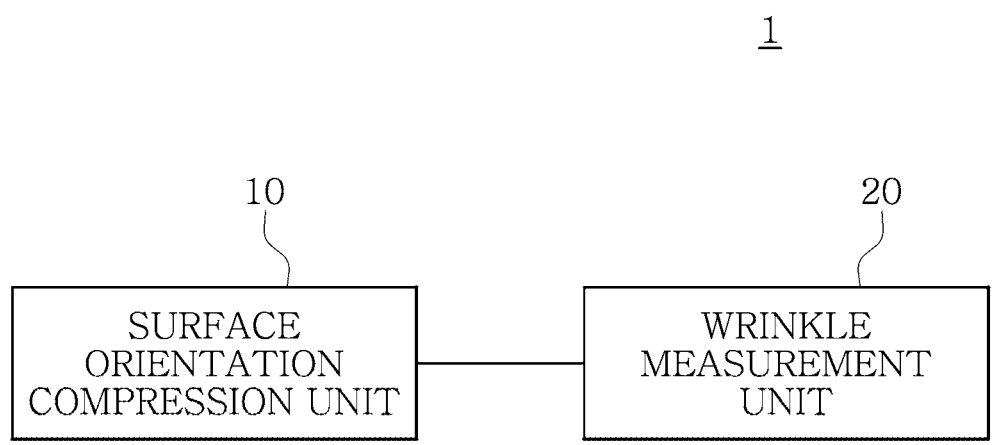

[FIG. 2A]
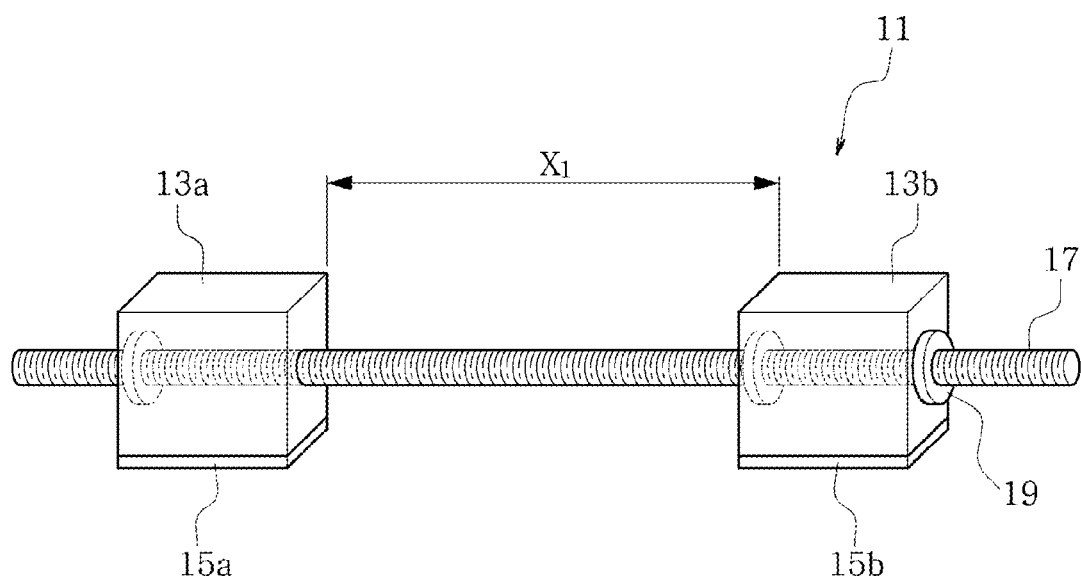
[FIG. 2B]
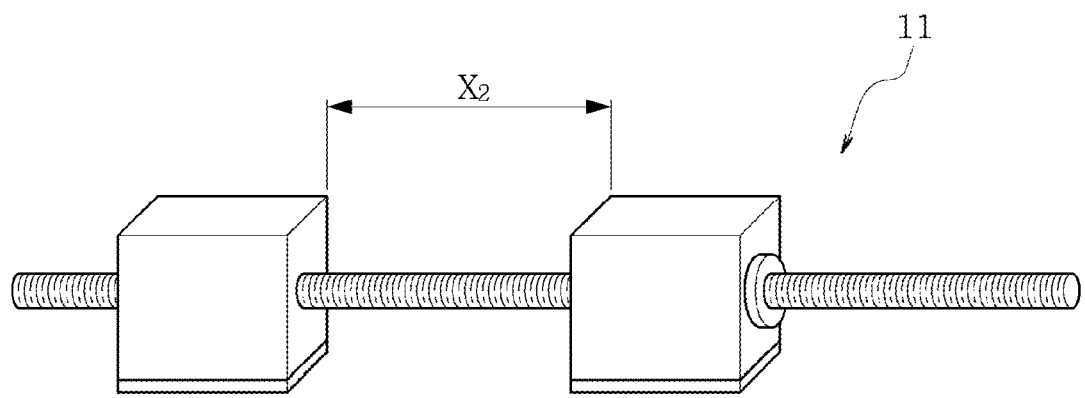

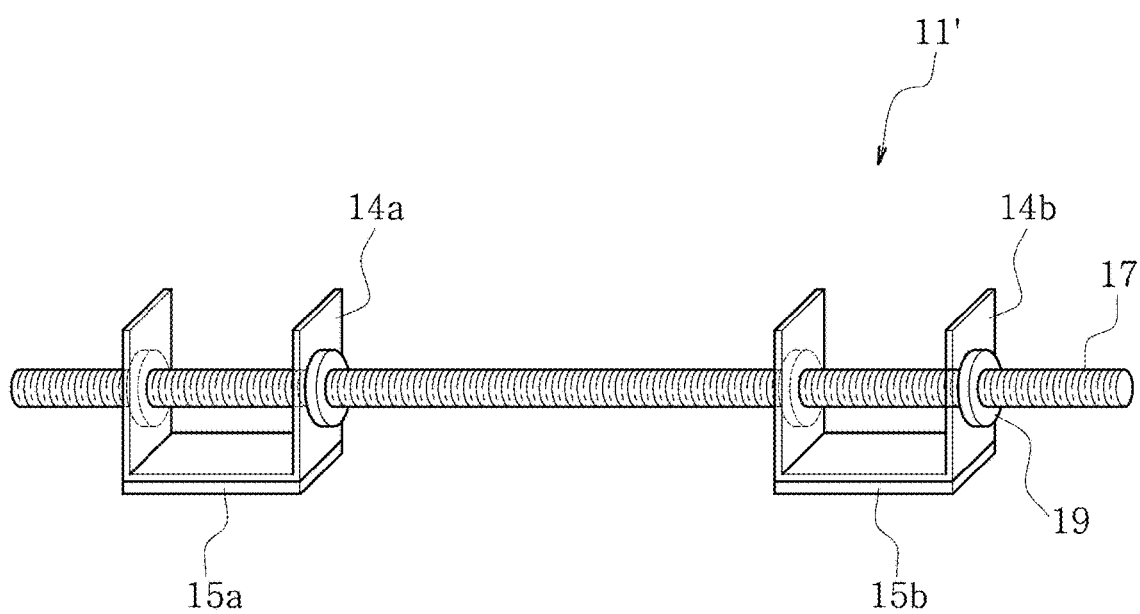
[FIG. 3]

【FIG. 4A】
【FIG. 4B】
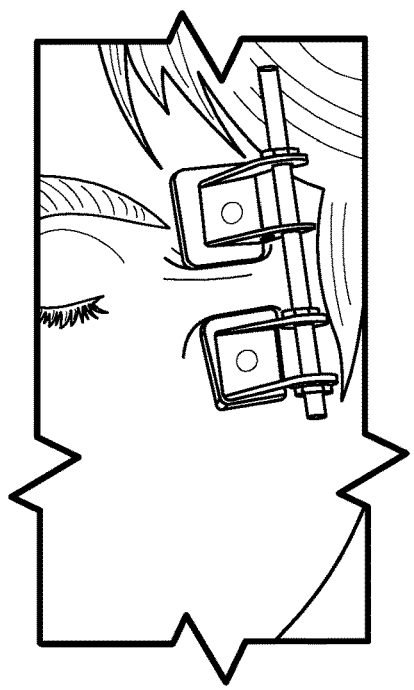

[FIG. 5]
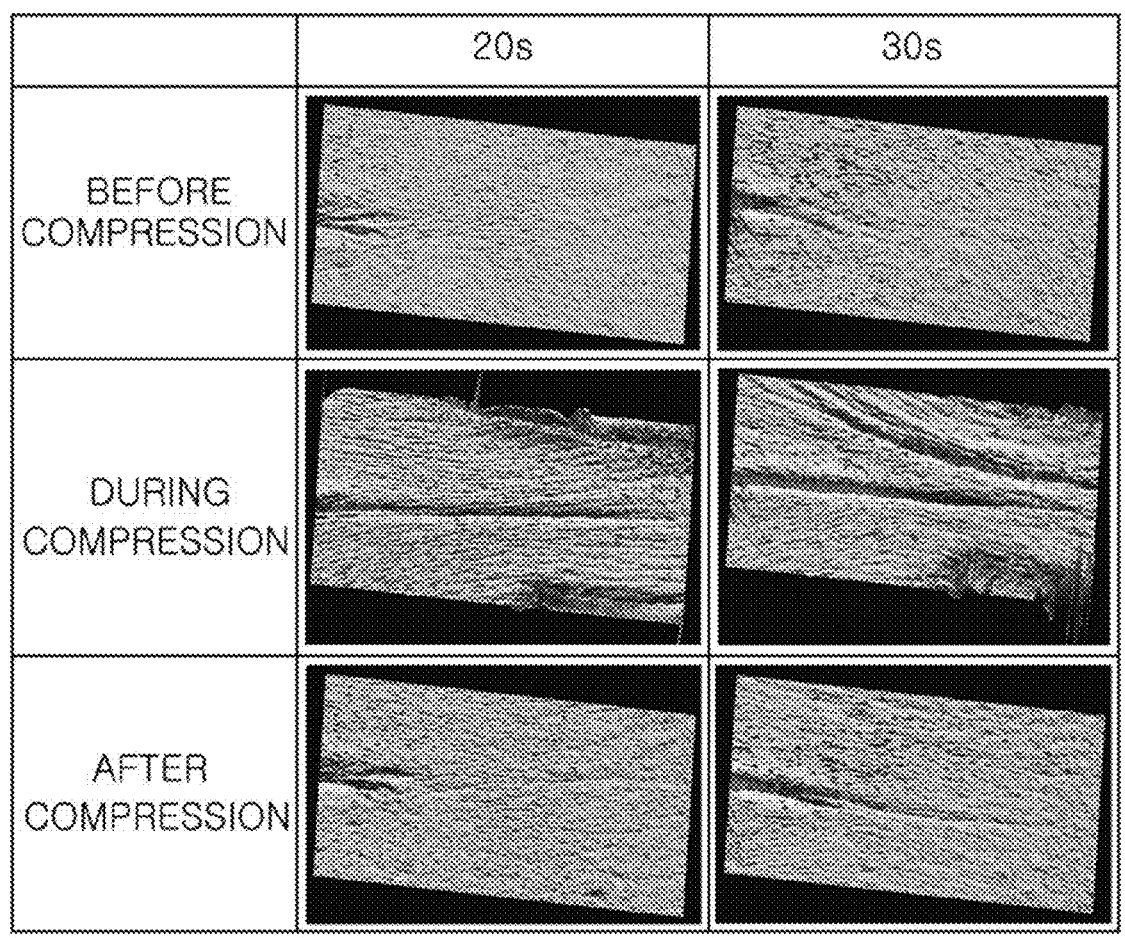

[FIG. 6]
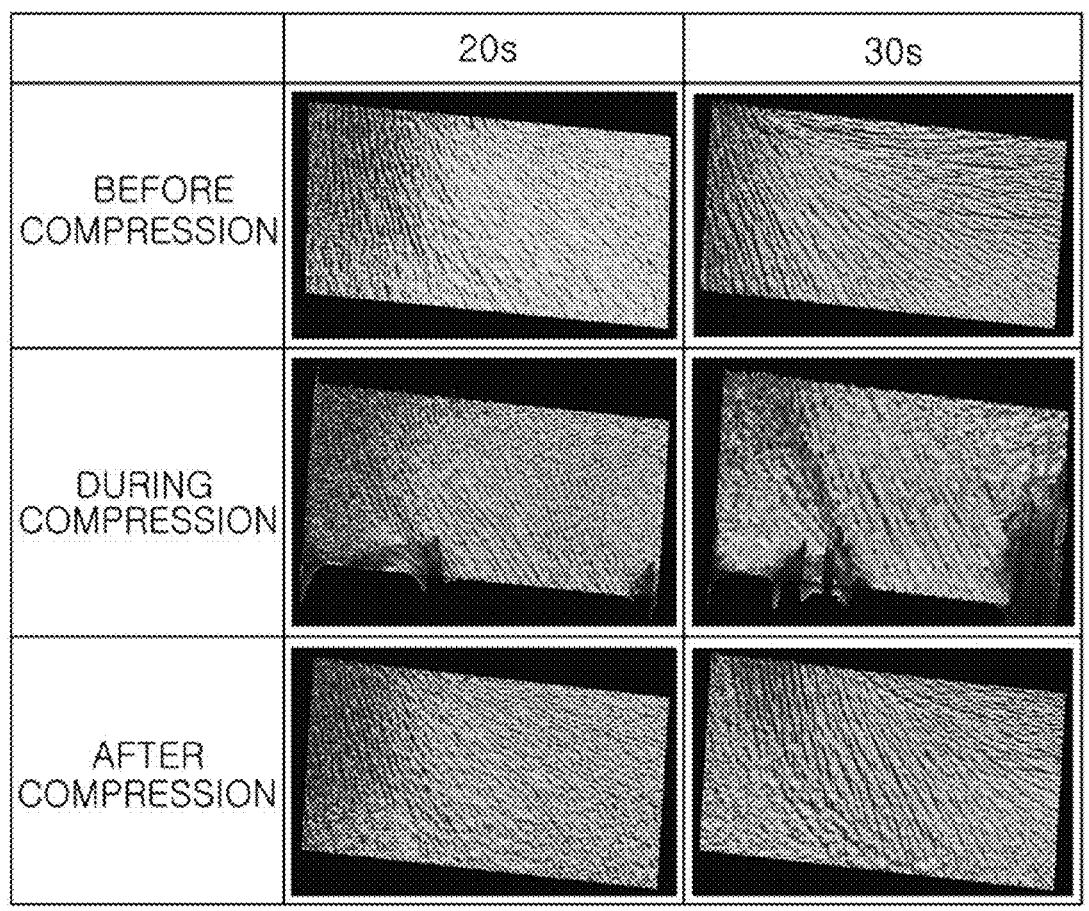

WRINKLE MEASUREMENT APPARATUS AND WRINKLE MEASUREMENT METHOD

TECHNICAL FIELD

The present disclosure relates to a wrinkle measuring device and a wrinkle measuring method, and more particularly, to a wrinkle measuring device and a wrinkle measuring method that can measure fine wrinkles invisible to the naked eyes and quantify the properties of wrinkles such as depth, shape and elasticity.

BACKGROUND ART

A noticeable first sign of aging is wrinkles. According to fine wrinkle classification, primary wrinkle refers to wrinkles of 20 to 100 μm, secondary wrinkle refers to wrinkles of 5 to 40 μm, tertiary wrinkle refers to wrinkles up to 0.5 μm, and quaternary wrinkle refers to wrinkles up to 0.05 μm.

Generally, there are many methods for measuring skin wrinkles.

Furthermore, as a method for measuring skin wrinkles, Patent Literature 1 discloses a method for measuring and analyzing skin wrinkles and aging status through a skin image.

In the case of the method for measuring and analyzing skin conditions through a skin image, a problem is that it is difficult to measure latent wrinkles which are likely to develop into primary wrinkle appearing more noticeable with age although not clearly visible. Wrinkles with a minimum depth of 1 mm can be visibly detected and allow image measurement. That is, secondary and subsequent wrinkles are impossible to measure by a method through a flat image.

Accordingly, there is a need for studies of a wrinkle measuring device and a wrinkle measuring method that can accurately analyze latent hidden fine wrinkles invisible to eyes.

DISCLOSURE

Technical Problem

The present disclosure is designed to solve the above problems, and therefore, the present disclosure is directed to providing a wrinkle measuring device and a wrinkle measuring method that can visibly compare and analyze secondary and subsequent wrinkles of less than 40 μm invisible to eyes.

Furthermore, the present disclosure is directed to providing a wrinkle measuring device and a wrinkle measuring method that can quantitatively analyze not only the features of wrinkles such as depth and shape but also the properties of wrinkles such as elasticity or resilience.

Technical Solution

To achieve the above object, a wrinkle measuring device according to an embodiment of the present disclosure includes a surface orientation compression unit including first and second contact units placed in close contact with skin at a preset interval to compress the skin toward the skin surface, and a wrinkle measurement unit configured to measure skin wrinkle in at least two of a state before compression, a state during compression, and a state after compression.

The wrinkle measurement unit may be a three-dimensional image measurement device.

The surface orientation compression unit includes the first and second contact units which can move between a first interval in non-compressed state and a second interval in compressed state, a through rod formed to pass through the first and second contact units, and position fixing units placed at one side or two sides of the first and second contact units on the through rod, such that the interval between the first and second contact units is the first interval or the second interval.

An adhesive or an adhesive tape may be formed on contact surfaces where the first and second contact units touch the skin.

A wrinkle measuring method according to an embodiment of the present disclosure includes compressing, by first and second contact units placed in close contact with skin at a preset interval, the skin toward the skin surface during a preset period of time by adjusting the interval between the first and second contact units, and measuring skin wrinkle in at least two of a state before compression of the skin, a state during compression of the skin, and a state after compression of the skin.

The measuring of skin wrinkle may include measuring at least one of an arithmetic average value of roughness profile, wrinkle shape, wrinkle depth, wrinkle area, wrinkle length, wrinkle volume, and the number of wrinkles.

The measuring of skin wrinkle may be performed through three-dimensional image measurement of the skin.

The skin elasticity may be measured based on a difference in wrinkle between before and after compression of the skin or between during and after compression of the skin.

The skin elasticity may be measured through measuring a restoration time taken for wrinkle after compression of the skin to return to a state before compression.

Through wrinkle measurement before and after compression of the skin, the wrinkle shape may be measured by compressing winkle of 40 μm or less before the compression.

Advantageous Effects

According to various embodiments of the present disclosure, there is provided a wrinkle measuring device and a wrinkle measuring method that can visibly compare and analyze secondary and subsequent wrinkles of less than 40 μm invisible to eyes.

Accordingly, latent hidden fine wrinkles invisible to eyes can be compared and analyzed.

Furthermore, there is provided a wrinkle measuring device and a wrinkle measuring method that can quantitatively analyze not only the features of wrinkles such as depth and shape but also the properties of wrinkles such as elasticity or resilience.

Accordingly, in wrinkle measurement and comparison, quantification can be achieved, allowing wrinkle analysis with accuracy and high reliability.

DESCRIPTION OF DRAWINGS

FIG. 1 is a diagram showing diagrammatically a wrinkle measuring device according to an embodiment of the present disclosure.

FIG. 2 is a perspective view showing a compression unit of a wrinkle measuring device according to an embodiment of the present disclosure.

FIG. 3 is a perspective view showing a compression unit of a wrinkle measuring device according to another embodiment of the present disclosure.

FIG. 4 is a photographic image showing a process of compressing wrinkles by a wrinkle measuring device according to an embodiment of the present disclosure.

FIG. 5 shows images of wrinkles around eyes measured by a wrinkle measuring device according to an embodiment of the present disclosure.

FIG. 6 shows images of wrinkles under eyes measured by a wrinkle measuring device according to an embodiment of the present disclosure.

BEST MODE

Hereinafter, a wrinkle measuring device and a wrinkle measuring method according to various embodiments of the present disclosure will be described with reference to FIGS. 1 through 6.

FIG. 1 is a diagram showing diagrammatically a wrinkle measuring device according to an embodiment of the present disclosure.

Referring to FIG. 1, the wrinkle measuring device 1 according to an embodiment of the present disclosure includes a surface orientation compression unit 10 (hereinafter also referred to as a "compression unit") including first and second contact units placed in close contact with the skin at a preset interval to compress the skin toward the skin surface, and a wrinkle measurement unit 20 to measure skin wrinkles in at least two of a state before compression, a state during compression, and a state after compression.

The surface orientation compression unit 10 is for compressing the skin toward the skin surface. The surface orientation compression unit 10 comes into close contact with the skin, and applies a predetermined pressure to the skin in the direction of skin surface to artificially create wrinkles.

Accordingly, the pressure is applied by the compression unit to wrinkles of 40 μm or less invisible to the naked eyes to form wrinkles of 40 μm or more, enabling comparison and analysis of the shape of wrinkles. Furthermore, wrinkles may be stimulated to measure elasticity or resilience of the skin (or wrinkles).

More specifically, the shape of wrinkles may be detected through wrinkle measurement, and at least one of the arithmetic average value of the roughness profile Ra, the wrinkle shape, the wrinkle depth, the wrinkle area, the wrinkle length, the wrinkle volume, and the number of wrinkles may be detected, but the present disclosure is not necessarily limited thereto.

The wrinkle measurement unit 20 is for measuring the shape of wrinkles as described above, and various processes can be used. At least one process of analysis through a two-dimensional (2D) image or a three-dimensional (3D) image, analysis through the area of shaded regions of wrinkles, and naked eye analysis may be used.

For the wrinkle measurement unit 20, a 3D image measurement device may be used. For example, in the case of a 3D image measurement device with fringe projection principle, accuracy in wrinkle assessment is high and high reproducibility of assessment can be achieved.

In the case of the 3D image measurement device, fine wrinkles of 9 to 12 μm in size may not be clearly visible when measured, but in the case of the present disclosure, compression or stimulation is applied to wrinkles using the compression unit 10 to make wrinkles more visible, thereby increasing the efficiency of 3D image measurement of wrinkles.

According to an embodiment of the present disclosure, for the 3D image measurement device, PRIMOS in Germany by GFM may be used. However, the present disclosure is not necessarily limited thereto, and various methods for 3D image measurement of wrinkles may be used.

FIG. 2 is a perspective view showing the surface orientation compression unit 10 according to an embodiment of the present disclosure, and FIG. 3 is a perspective view showing the surface orientation compression unit 10 according to another embodiment of the present disclosure.

Referring to FIG. 2, a surface orientation compression unit 11 includes a first contact unit 13a, a second contact unit 13b, a through rod 17, and position fixing units 19.

A first interval X1 in non-compressed state ((A) of FIG. 2) or a second interval X2 in compressed state ((B) of FIG. 2) may be formed between the first and second contact units 13a and 13b. The first and second contact units 13a and 13b may be placed in close contact with the skin at a preset interval to compress the skin toward the skin surface.

Specifically, the first and second contact units 13a and 13b may be formed moveably between the first interval X1 in non-compressed state and the second interval X2 in compressed state. For example, if the first interval X1 is 3 cm, the second interval X2 may be 2 cm.

The through rod 17 is formed to pass through the first and second contact units 13a and 13b. The plurality of position fixing units 19 for fixing the first and second contact units 13a and 13b may be mounted on the through rod 17.

The position fixing units 19 placed at one side or two sides of the first and second contact units 13a and 13b on the through rod 17 may be adapted, such that the interval between the first and second contact units 13a and 13b is the first interval X1 or the second interval X2.

In the case of the embodiments of FIGS. 2 and 3, it is shown that the through rod 17 has a screw thread to receive a nut, and for the position fixing units 19, a nut is used. However, the present disclosure is not necessarily limited thereto, and it is obvious that the present disclosure may be configured to fix the first and second contact units 13a and 13b on the through rod 17 in another manner. For example, the first and second contact units may be fixed on the unthreaded through rod using a rubber ring.

On the other hand, an adhesive or an adhesive tape 15a and 15b may be formed on contact surfaces where the first and second contact units touch the skin. By improving the adhesion of the contact surfaces that touch the skin, the pressure can be stably applied to the skin. For reference, although the embodiments of FIGS. 2 and 3 show that a both-sided tape is formed on the contact surfaces, the present disclosure is not necessarily limited thereto, and various members that can impart an adhesive strength may be used.

In the case of the compression unit 11 of the embodiment of FIG. 2, the first and second contact units 13a and 13b have a rectangular parallelepiped shape, while in the case of the compression unit 11' of the embodiment of FIG. 3, the first and second contact units 14a and 14b include a contact plate and two side plates connected thereto.

As shown in the embodiments of FIGS. 2 and 3, the shape of the first and second contact units 13a and 13b may have various shapes including the contact surfaces that come into close contact with the skin.

FIG. 4 is a photographic image showing a state before applying the pressure in the direction of skin surface (A) and a state in which the pressure is applied (B) according to an embodiment of the present disclosure.

The first and second contact units 13a, 13b, 14a, 14b are attached to the skin surface and apply the pressure in the direction of skin surface. The pressure may be adjusted by adjusting the first interval X1 and the second interval X2, and after the pressure is applied during a preset period of time, the pressure may be removed from the skin surface. According to an embodiment, the pressure may be applied for 3 minutes, and then, the compression unit may be separated from the skin.

Particularly, the magnitude of pressure or the extent of pressure may be adjusted by adjusting the period of time during which the pressure is applied or a difference between the first interval and the second interval.

Hereinafter, a wrinkle measuring method according to an embodiment of the present disclosure is described in detail. Like features may be applied to like members and methods of the wrinkle measuring device.

The wrinkle measuring method according to an embodiment of the present disclosure enables first and second contact units placed in close contact with the skin at a preset interval to compress the skin toward the skin surface for a preset period of time by adjusting the interval between the first and second contact units, and measures skin wrinkles in at least two of a state before compression of the skin, and a state during compression of the skin, and a state after compression of the skin.

The measuring of skin wrinkles may measure at least one skin morphology of the arithmetic average value of the roughness profile, the wrinkle shape, the wrinkle depth, the wrinkle area, the wrinkle length, the wrinkle volume, and the number of wrinkles. The present disclosure is not necessarily limited thereto, and various parameters may be applied thereto.

According to an embodiment of the present disclosure, for skin wrinkle measurement, various processes including 2D image measurement, 3D image measurement, calculation of the area of shaded regions of wrinkles, and naked eye measurement may be applied thereto.

Particularly, the measuring of skin wrinkles may be performed through 3D image measurement of the skin. Through 3D image measurement, the wrinkle depth, the arithmetic average value of the roughness profile, the wrinkle shape, the wrinkle area, the wrinkle length, the wrinkle volume, and the number of wrinkles can be measured by one time measurement, and analysis of various features of wrinkles can be conducted by only one time measurement.

According to an embodiment of the present disclosure, skin elasticity or skin resilience can be measured through wrinkle measurement. More specifically, the elasticity of wrinkles or the resilience of wrinkles can be measured. That is, the elasticity of wrinkles may be a factor that can determine how much high speed wrinkles will develop.

Accordingly, elasticity of the skin (or wrinkles) or resilience of the skin (or wrinkles) may be measured through how fast the skin is restored. To this end, it is important to know how fast the skin is restored and the extent at which the skin is restored (for the same period of time).

More specifically, elasticity of the skin (or wrinkles) may be measured based on a difference in wrinkles between before and after compression of the skin or between during and after compression of the skin. That is, through measurement before/after compression, elasticity of the skin (or wrinkles) may be measured by measuring how many wrinkles are formed by the pressure and how deeply wrinkles are formed. Furthermore, through a difference in wrinkles between during and after compression, skin elasticity may be measured by measuring how much the skin is restored.

Furthermore, elasticity of the skin (or wrinkles) may be measured through measuring before compression of the skin and the restoration time of wrinkles after compression over time. That is, elasticity of the skin (or wrinkles) may be measured by measuring the restoration time taken for wrinkles after compression to return to the original state (the state before compression).

According to the embodiments of the present disclosure, skin elasticity is measured in the form of time or length or area, allowing quantitative assessment. That is, the degree of elasticity of the skin (or wrinkles) may be determined through quantitative comparison and analysis by comparing and analyzing time values or length or area values.

Through wrinkle measurement before and after compression of the skin, the wrinkle shape may be measured by compressing wrinkles of 40 μm or less before compression.

That is, in the case of wrinkles of 40 μm or less, it is impossible to detect by the eyes. Furthermore, in this case, even though 3D imaging is performed, accurate analysis may be infeasible. Accordingly, in the case of the present disclosure, the wrinkle shape can be accurately analyzed through wrinkle measurement before and after compression.

Particularly, fine wrinkles invisible to eyes in 20s and 30s can be accurately compared and analyzed.

In the end, according to an embodiment of the present disclosure, stimulation is delivered to wrinkles to make the wrinkles look noticeably visible and the wrinkle shape is measured, so latent hidden fine wrinkles invisible to eyes can be accurately measured. Furthermore, because comparison is made under compression of the same pressure, quantitative comparison and analysis of wrinkles can be conducted by analyzing the morphology of wrinkles in compressed state.

[Embodiment 1]

Two persons in each age group of 20s and 30s (a total of 4) were allowed to wash their faces with soap and then adapt the skin for 15 minutes under the constant temperature/constant humidity conditions (20° C., RH 40%). Before applying the compression unit to the skin, 3D imaging was performed using a 3D measurement system (PRIMOS in Germany by GFM). Subsequently, the first and second contact units of the compression unit were attached to the skin around and under eyes with a both-sided adhesive tape. The interval between the first and second contact units before compression, i.e., the first interval X1 was set to 3 cm, and the interval between the first and second contact units after compression, i.e., the second interval X2 was set to 2 cm. After the compressed state was maintained for 3 minutes, the compression unit was detached. Then, the skin around and under eyes were imaged using the same 3D measurement system. The images measured around eyes are shown in FIG. 5, and images measured under eyes are shown in FIG. 6.

Furthermore, the arithmetic average value of the roughness profile Ra analyzed through the 3D images is as shown in Table 1.

TABLE 1

| | Around eyes | | | Under eyes | | |
|---|---|---|---|---|---|---|
| | Before compression (μm) | During compression (μm) | After compression (μm) | Before compression (μm) | During compression (μm) | After compression (μm) |
| 20s | 15.4 | 104.9 | 20.35 | 20.4 | 39.1 | 25.4 |
| 30s | 26.9 | 131.5 | 32.9 | 26.85 | 76.4 | 46.2 |

Referring to the above table 1, as a result of measurement and analysis using the wrinkle measuring device according to an embodiment of the present disclosure, secondary wrinkles in 20s and 30s turned to tertiary wrinkles during compression, and after removing compression, wrinkles increased in comparison to before compression. In the case of 20s, invisible wrinkles turned to visible wrinkles.

Particularly, in the case of the skin under eyes where the thickness of the skin is thin, a difference in the arithmetic average value of the roughness profile Ra between 20s and 30s was about 5 μm before inducing wrinkles by the compression unit, but a difference of about 20 μm was created after inducing wrinkles by the compression unit. That is, the difference is about four times larger than before applying the pressure to wrinkles by the compression unit.

Through this embodiment, it was possible to detect invisible fine wrinkles by the eyes, and quantitatively indicate and compare the numerical values of wrinkles.

The invention claimed is:

1. A wrinkle measuring device, comprising:
a skin compressor comprising first and second contact units placed in close contact with skin at a preset interval to compress the skin toward the skin surface to create wrinkles artificially; and
a three-dimensional image measurement device configured to measure skin wrinkle by three-dimensional image measurement of the skin in at least two of a state before compression of the skin, a state during compression of the skin by the skin compressor, and a state after compression of the skin by the skin compressor; and
wherein the three dimensional image measurement device measures skin elasticity in a form of time or length or area based on
a difference in a length or an area of wrinkle between before and after compression of the skin by the skin compressor or between during and after compression of the skin by the skin compressor, or
a restoration time taken for wrinkle after compression of the skin by the skin compressor to return to a state before compression.

2. The wrinkle measuring device according to claim 1, wherein the skin compressor comprises:
the first and second contact units which can move between a first interval in non-compressed state and a second interval in compressed state;
a through rod formed to pass through the first and second contact units; and
position fixing units placed at one side or two sides of the first and second contact units on the through rod, such that the interval between the first and second contact units is the first interval or the second interval.

3. The wrinkle measuring device according to claim 2, wherein an adhesive or an adhesive tape is formed on contact surfaces where the first and second contact units touch the skin.

4. A wrinkle measuring method, comprising:
compressing, by first and second contact units placed in close contact with skin at a preset interval, the skin toward the skin surface during a preset period of time to create wrinkles artificially by adjusting the interval between the first and second contact units;
measuring skin wrinkle by three-dimensional image measurement of the skin in at least two of a state before compression of the skin, a state during compression of the skin by the first and second contact units, and a state after compression of the skin by the first and second contact units, a state after compression of the skin by the first and second contact units, and skin elasticity based on
a difference in a length or an area of wrinkle between before and after compression of the skin by the first and second contact units or between during and after compression of the skin by the first and second contact units, or
a restoration time taken for wrinkle after compression of the skin by the first and second contact units to return to a state before compression.

5. The wrinkle measuring method according to claim 4, wherein the measuring of skin wrinkle comprises measuring at least one of an arithmetic average value of roughness profile, wrinkle depth, wrinkle area, wrinkle length, wrinkle volume, and the number of wrinkles.

6. The wrinkle measuring method according to claim 4, wherein through wrinkle measurement before and after compression of the skin by the first and second contact units, wrinkle shape is measured by compressing wrinkle of 40 μm or less before the compression.

* * * * *